United States Patent [19]

Prinzbach et al.

[11] 4,116,984

[45] Sep. 26, 1978

[54] MANUFACTURE OF ISOMERIC 1,4-DIBROMO-EPOXY-CYCLOHEXENES

[75] Inventors: Horst Prinzbach; Reinhard Schwesinger, both of Freiburg, Fed. Rep. of Germany

[73] Assignee: BASF Aktiengesellschaft, Ludwigshafen, Fed. Rep. of Germany

[21] Appl. No.: 710,459

[22] Filed: Aug. 2, 1976

[30] Foreign Application Priority Data

Aug. 23, 1975 [DE] Fed. Rep. of Germany ....... 2537681

[51] Int. Cl.$^2$ .................. C07D 303/08; C07D 301/32
[52] U.S. Cl. ........................ 260/348.12; 260/348.51; 260/348.53; 260/348.54; 260/348.55; 260/348.36
[58] Field of Search ........... 260/348 C, 348.12, 348.51

[56] References Cited

PUBLICATIONS

Houben–Weyl, Methoden der Organischen Chemie, vol. I/1 (1958), pp. 362, 379.
Angewandte Chem. internat. Edit., vol. 11 (1972), No. 10, pp. 935–943.
R. Schwesinger, Dissertation, Universitat Freiburg 1975.

*Primary Examiner*—Norma S. Milestone
*Attorney, Agent, or Firm*—Keil, Thompson & Shurtleff

[57] ABSTRACT

The manufacture of pure isomeric 1,4-dibromo-epoxy-cyclohexenes and their derivatives, which are starting compounds for units used to synthesize neutral compounds, e.g. cyclitols or aminocyclitols.

6 Claims, No Drawings

MANUFACTURE OF ISOMERIC 1,4-DIBROMO-EPOXY-CYCLOHEXENES

The present invention relates to the manufacture of pure isomeric 1,4-dibromo-epoxy-cyclohexenes, of which three isomeric forms exist in respect of the spatial configuration of the two bromine atoms.

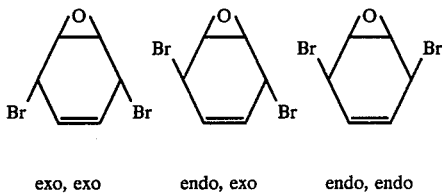

exo, exo     endo, exo     endo, endo

In the process according to the invention for the manufacture of the isomeric 1,4-dibromo-epoxy-cyclohexenes in a pure or concentrated form from an isomer mixture obtained on bromination of 4,5-epoxy-cyclohexene, the endo/exo and/or exo/exo and/or endo/endo compound is deliberately isolated by fractional crystallization of the above isomer mixture from an organic solvent, with or without first setting up isomerization equilibria in the mixture.

The bromination of 4,5-epoxy-cyclohexene to 1,4-dibromo-epoxy-cyclohexene per se has been disclosed. In a particularly advantageous embodiment of the bromination, the reaction is carried out with two equivalents of N-bromosuccinimide in anhydrous carbon tetrachloride in the presence of a catalytic amount of azobisisobutyronitrile at the boiling point of carbon tetrachloride, ethylene being passed through the reaction mixture to prevent side-reactions, and the reaction being terminated after from 3.5 to 4 hours. After cooling the mixture, the succinimide is filtered off, the reaction solution is advantageously purified over a column filled with silica gel, and the solvent is advantageously distilled off under reduced pressure.

The bromination gives an isomer mixture of varying composition which contains, for example, about 40% of exo, exo, about 56% of exo, endo and about 4% of endo, endo compounds.

To crystallize the endo, exo compound, the crude mixture is dissolved in trichloroethylene. Advantageously, from 3 to 5 parts by weight of trichloroethylene are used per part by weight of epoxycyclohexene employed for the bromination. On leaving the mixture to stand at from −5° to −15° C., endo, exo-1,4-dibromo-epoxy-cyclohexene crystallizes out.

Advantageously, the cooled solution is, in this process, seeded with a small amount of the endo, exo compound to initiate the crystallization. It is particularly advantageous to agitate the solution or suspension during the crystallization. For this purpose it is possible to use, for example, mechanical stirrers, e.g. magnetic stirrers, vibro-mixers or ultrasonics.

The crystallization of the endo, exo compound is in general complete after from 2 to 24 hours. The product is filtered off and the exo, exo compound is allowed to crystallize out as a second fraction by leaving the mother liquor to stand at from −20° to −30° C.

Advantageously, the solution is, in this process, seeded with a small amount of exo, exo compound, and advantageously petroleum ether is added to the solution. The petroleum ether is used in such amount that at −65° C. the solution just turns cloudy. The crystals of the exo, exo compound are filtered off and are advantageously washed with trichloroethylene/petroleum ether.

The respective crystal fractions of endo, exo compound and exo, exo compound obtained under the stated conditions of the invention are virtually pure.

One or more crystal fractions can be obtained from the mother liquor at from −50° to −70° C. after seeding and, if necessary, after adding petroleum ether until the mixture begins to turn cloudy; in most cases, these crystal fractions can only be separated into the individual isomers after laborious fractional crystallization.

The present invention further relates to the setting up of isomerization equilibria in a mixture of the three dibromides in an organic solvent in the presence of a catalytic amount of a soluble organic or inorganic bromide salt, for the purpose of increasing the proportion of a particular isomer and causing its crystallization.

In general, saturated solutions of any particular isomer mixture are prepared at room temperature, from 0.5 to 3% by weight, based on the isomer mixture, of a soluble bromide salt are added and the mixture is left to stand at room temperature until the isomerization equilibrium is set up.

The rate at which the equilibrium is set up depends on the solvent used and can be followed in a simple manner by thin layer chromatography on silica gel, with benzene as the migrating agent.

After the particular equilibrium has been set up, the bromide salt used is as a rule removed by converting it to an aqueous solution, and the isomer mixture is subjected to fractional crystallization.

Suitable organic solvents for setting up the equilibrium are, in particular, chlorinated hydrocarbons, e.g. methylene chloride, chloroform or carbon tetrachloride, cyclic aliphatic ethers, e.g. tetrahydrofuran, esters or nitriles of lower aliphatic carboxylic acids, e.g. ethyl acetate or acetonitrile, lower alcohols or ketones, e.g. methanol or acetone, and aromatic hydrocarbons, especially benzene.

Bromide salts, soluble in organic solvents, which can be used are, preferably, tetraalkylammonium salts with lower alkyl radicals of 1 to 5 carbon atoms. Amongst these, the following should be mentioned in particular: tetramethylammonium bromide, tetraethylammonium bromide, tetra-n-propylammonium bromide and tetra-n-butylammonium bromide.

However, depending on the solvent employed, it is also possible to use, for example, lithium bromide or benzyltrialkylammonium bromides.

Table 1 shows the percentage composition of isomerization equilibria of the three isomeric dibromides in various solvents.

TABLE 1

| Isomerization equilibria of the dibromides (%) | | | | |
|---|---|---|---|---|
| | exo,exo | endo,exo | endo,endo | |
| $CCl_4$ | 30 | 65 | 5 | IV |
| $C_6H_6$ | 14 | 67 | 19 | IV |
| $CHCl_3$ | 20.5 | 65 | 14.5 | II |
| $CH_2Cl_2$ | 28 | 52 | 20 | II |
| THF | 31 | 52 | 17 | IV |
| Methyl acetate | 22 | 62 | 16 | III |
| $(CH_3)_2CO$ | 0 | 80 | 20 | III |
| $CH_3CN$ | 0 | 59 | 41 | II |
| $CH_3OH$ | 11 | 67 | 22 | I |
| undiluted (80° C) | 28 | 52.5 | 19.5 | IV |
| I $(CH_3)_4N^{30}Br^-$ | | | | |
| II $(C_2H_5)_4N^+Br^-$ | | | | |
| III $(n-C_3H_7)_4N^+Br^-$ | | | | |
| IV $(n-C_4H_9)_4N^+Br^-$ | | | | |

It can be seen from the Table that after setting up the isomerization equilibrium, for example in methylene chloride, carbon tetrachloride or tetrahydrofuran, a high proportion of exo, exo compound is present. Hence, in these solvents, the proportion of the exo, exo compound can be increased when starting from isomer mixtures with low contents of exo, exo compound, and, if desired, the exo, exo compound can be concentrated to above 70% by crystallizing out the two other isomers in carbon tetrachloride at room temperature from about 25 percent strength by weight solution.

In acetone, the proportion of the endo, exo compound can be increased to 80%.

In acetonitrile, surprisingly, over 40% of the endo, endo compound are present. The process according to the invention for the first time permitted the preparation of endo, endo-1,4-dibromo-epoxy-cyclohexene by setting up the isomerization equilibrium in acetonitrile, distilling off the solvent, separating off the bromide salt used by converting it to an aqueous phase, and recrystallizing from carbon tetrachloride.

Advantageously, a solution, of from 10 to 25 percent strength by weight, of an isomer mixture in acetonitrile, is mixed with the appropriate catalytic amount of tetraalkylammonium bromide and is left to stand at room temperature to set up the isomerization equilibrium. After distilling off the solvent under reduced pressure, the tetraalkylammonium bromide used is separated off, advantageously by converting the mixture of the dibromides to an ether or methylene chloride phase and the bromide salt into an aqueous phase, and separating off the latter. The organic solvent is distilled off and the pure endo, endo compound is obtained in a crystalline form from a solution, of from 7 to 14 percent strength by weight, of the residue in carbon tetrachloride at from 15° to 25° C., advantageously while stirring.

Of course, the residues of mother liquors can also be subjected to a renewed isomerization. Depending on the desired isomer, it is possible, for example, to subject the mixture, obtained from the bromination, to the isomerization conditions without first isolating the endo, exo and/or exo, exo compound. From the point of view of the intended further reactions, the exo, exo and endo, endo isomers are the preferred compounds, so that it is also possible, for example, to isomerize pure endo, exo fractions, or fractions containing a greatly increased proportion of the endo, exo compound, to the former isomers.

The bromide salt used is separated off in the manner described above. The preferred solvent for recrystallizing an isomer mixture, after setting up an isomerization equilibrium, in order to isolate a pure exo, exo or endo, endo compound is carbon tetrachloride.

The pure isomeric 1,4-dibromo-epoxy-cyclohexenes are valuable starting compounds for the controlled manufacture of substituted sterically pure 6-membered ring compounds, especially of cyclitols, aminocyclitols or their derivatives, which are constituents of natural compounds, e.g. antibiotics.

The preparation of the isomeric 1,4-dibromo-epoxy-cyclohexenes in a pure form, in accordance with the invention, provides, for the first time, the preconditions for reactions to form a plurality of compounds. For example, replacement reactions of the bromine atoms, reactions at the double and/or at the epoxide ring, and other reactions, can be carried out. Thus, for example, a more advantageous method is provided for obtaining compounds which are structural units of natural compounds, e.g. antibiotics, which can be used for the chemical or microbiological synthesis of these.

Thus, for example, streptamine and streptidine, which can be prepared from streptamine, may be used to synthesize dihydrostreptomycin, as is described by S. Umezawa et al. in J. Amer. Chem. Soc. 96, (1974), 920–21. For example, streptamine can also, for example, be added to the nutrient media of micro-organisms which synthesize antibiotic compounds, as is described, for example, in the book Structures and Syntheses of Aminoglycoside Antibiotics by S. Umezawa in Advances in Carbohydrate Chemistry and Biochemistry, volume 30 (1974), pages 111 et seq., Academic Press, or by W. Thomas Shier et al. in Proceedings of the National Academy of Science 63, (1969), 198–204.

The reaction of exo, exo-1,4-dibromo-epoxy-cyclohexene with potassium permanganate can be used to produce a high yield of the sterically pure dibromo-dihydroxy-cyclohexane-epoxide compound, from which cis-benzene trioxide is readily accessible (Angew. Chem. 84, (1972), 990 et seq.). Cis-benzene-trioxide has recently become a starting compound for numerous interesting compounds, e.g. for the preparation of streptamine. As a further example, cis-benzene-trioxide can be converted to the natural compound chiro-inositol by simple hydrolysis with acid.

3,6-Endo, endo-dibromo-4,5-epoxy-cyclohexene is the starting compound for trans-benzene-trioxide, to which it is converted by replacing the two bromine atoms by acetyl radicals, introducing two hydroxyl groups at the double bond by means of potassium permanganate, esterifying these groups by the tosyl radical, splitting off the acetyl groups and obtaining trans-benzene-trioxide by reacting the product with monosodium glycollate in the presence of basic aluminum oxide in anhydrous tetrahydrofuran. Trans-benzene-trioxide, in turn, is a starting compound for novel syntheses.

As a further example of a reaction of endo, endo-1,4-dibromo-epoxy-cyclohexene, 1,2:4,5-dianhydro-3,6-dibromo-3,6-didesoxy-cis-inositol can be prepared therefrom by reaction with a per-acid. This compound, on reaction with tetramethylammonium formate, gives the 3,6-di-O-formyl compound. After splitting off the formyl radicals with methanolic ammonia solution, 1,2:4,5-dianhydro-muco-inositol, a known compound, is obtained, from which the antibiotic structural units epistreptamine and actinamine are obtained by reaction with hydrazine and N,N'-dimethylhydrazine, respectively.

By using mutant micro-organisms, which only produce antibiotics if certain aminocyclitols, such as 2-desoxystreptamine, are added to the nutrient solution, it is possible to product new semisynthetic aminoglycoside antibiotics.

Thus, for example, using the Streptomyces fradiae mutant ATCC 21,401 and adding streptamine or epistreptamine to the nutrient solution, the neomycin-analog antibiotic hybrimycin A1 and A2 and hybrimycin B1 and B2 are obtained respectively (U.S. Pat. No. 3,669,838), whilst using the 2-desoxystreptamine-negative mutant ATCC 14,827 of the paromomycin-producing strain Streptomyces rimosus forma paromomycinus, the paromomycin-analogs hybrimycin C1 and C2 are obtained by addition of streptamine (Shier et al., Biochemistry 13 (1974), 5,073).

In the same way, it is possible, by means of mutant microorganisms, to replace the 2-desoxystreptamine, in amino-glycoside antibiotics which contain 2-desoxystreptamine as a structural unit, by epistreptamine (Kojima and Satoh, Journal of Antibiotics 26 (1973), 784) or actinamine.

Other reactions of the 1,4-dibromo-epoxy-cyclohexenes, e.g. with tetramethylammonium benzoate, can be used to produce sterically pure compounds in which the bromine atoms have been replaced. The bromine atoms can also be replaced by, e.g., acetyl, formyl or, indirectly, by hydroxyl. The corresponding epoxy-cyclohexene-diols offer a simple method of obtaining good yields of conduritols and conduramine, by opening the epoxide ring by bases or amines, respectively.

In the Examples which follow, the nomenclature corresponding to the IUPAC rules is used in addition to the designations exo and endo. Parts are by weight.

EXAMPLE 1

4,5-Epoxycyclohexene 320 g of cyclohexa-1,4-diene (about 90% pure) are dissolved in 400 ml of ether and 380 g of 40% strength peracetic acid are added dropwise, whilst cooling with ice. The solution should be homogeneous after completion of the addition; if not, ether should be added until it is completely homogeneous. After a reaction time of about 40 hours at 0°–5° C., the mixture is poured into ice water and extracted with 500 ml of ether, and the organic phase is extracted with 600 ml of ice-cold 10% strength potassium hydroxide solution which contains potassium sulfite (the wash water being tested for excess alkali with pH paper and the organic phase being tested for excess peracetic acid with KI/acetic acid). The low-boiling solvents are first distilled off through a column, under atmospheric pressure, excess cyclohexa-1,4-diene is then distilled off and lastly, the product is distilled under reduced pressure from a waterpump (boiling point 40° C./12 mm Hg).

Yield: 200 g (> 95%, based on cyclohexadiene converted).

Note: The product must be substantially free from cyclohexadiene before it is converted further, since otherwise HBr is liberated during the allyl bromination. The compound is sufficiently pure if cyclohexadiene is no longer detectable, e.g. in the NMR spectrum.

EXAMPLE 2

Bromination of 4,5-epoxycyclohexene and fractional crystallization 96 g of 4,5-epoxycyclohexene and 1.2 l of absolute carbon tetrachloride are mixed in a 2 l three-necked flask equipped with a stirrer, gas inlet tube, efficient column and distillation attachment with contact thermometer (set to 73.5° C.). 200 ml of carbon tetrachloride are distilled off slowly in order azeotropically to remove residual water in the epoxide. 350 g of N-bromosuccinimide which has been dried over KOH and then over phosphorus pentoxide under reduced pressure from a rotary vane pump at room temperature, but which has not been recrystallized, are then added, followed by 1 g of azobisisobutyronitrile, and a slight stream of ethylene is passed into the mixture throughout the reaction (at the rate of about 1 bubble per second). As soon as the air has been displaced, the mixture is heated to just the right degree that after the reaction has started the solvent distils off slowly, drop by drop (about 100 ml/hour). Because of the decreasing heat of reaction, the heating is continuously readjusted by the contact thermometer circuit. The reaction is terminated after 3.5–4 hours. The mixture is allowed to cool to 0° C., the succinimide is filtered off and the reaction solution is purified over a column of 300 g of silica gel, elution being carried out immediately with 0.75 l of carbon tetrachloride or with 0.5 l of trichloroethylene, and the solvent being evaporated off under reduced pressure.

The residue obtained is dissolved in 250 ml of trichloroethylene and after seeding with endo, exo-dibromo compound, the mixture is left for 2 hours at −10° C., whilst being stirred. The crystal mass which has separated out is filtered off and 55 g of endo, exo-dibromo compound of melting point 118° C. are obtained.

Just sufficient petroleum ether is added to the mother liquor that no cloudiness occurs at −60° C., and the mixture is left to stand for 24 hours at −20° C. in order to crystallize the exo, exo-dibromo compound. The latter is filtered off, and the crystals are rinsed with a trichloroethylene/petroleum ether mixture which has been cooled to a low temperature. If necessary, the product is recrystallized from a trichloroethylene/petroleum ether mixture. 20 g of exo, exo-dibromo compound of melting point 98° C. are obtained.

After seeding with all three isomers, the mother liquor is left to stand for several days longer, at −60° C. 55 g of a mixture which is difficult to separate and consists of 19 g of endo, exo-dibromo compound, 32 g of exo, exo-dibromo compound and 4 g of endo, endo-dibromo compound, as determined by integration of the NMR spectrum (benzene) are obtained.

EXAMPLE 3

Setting up the equilibrium in order to increase the proportion of exo, exo-dibromide.

The endo, exo-dibromo compound is dissolved in the minimum amount of methylene chloride, 1% by weight of tetraethylammonium bromide, based on the amount of dibromo compound employed, is added, and the mixture is left to stand at 20° C. After the equilibrium has been set up (as confirmed by thin layer chromatography, using silica gel/benzene), the mixture is extracted by shaking four times with an equal volume of water and the organic phase is concentrated to dryness under reduced pressure. The residue is dissolved in warm carbon tetrachloride, using 3.2 parts of the latter per part of residue, and the solution is left to crystallize at 20° C. The mixture — comprising 0.6 part — which has crystallized out, and which consists of endo, exo-dibromo compound and endo, endo-dibromo compound, is filtered off and can be recycled. The mother liquor is concentrated to dryness under reduced pressure. The residue obtained — 0.4 part — has approximately the following composition: 70% of exo, exo-dibromo, 23% of endo, exo-dibromo and 7% of endo, endo-dibromide.

EXAMPLE 4

Setting up the equilibrium to increase the proportion of, and isolate, the endo, endo-dibromide 254 g of an isomer mixture according to Example 2, representing the residue of the mother liquor after separating off the endo, exo-dibromo compound and exo, exo-dibromo compound, are dissolved in 2 l of acetonitrile, 0.5% by weight, based on the isomer mixture, of tetraethylammonium bromide is added, and the mixture is left at 20° C. until the equilibrium has been set up (as confirmed by thin layer chromatography, using silica gel/benzene). The solvent is the distilled off under reduced pressure, water is added to the residue, the mixture is extracted by shaking with ether, the ether phase is dried and the ether is distilled off under reduced pressure. The residue, in 3 l of carbon tetrachloride, is left at 22° C., whilst being stirred, in order to crystallize. 70 g of endo, endo-dibromo compound of melting point 134°-5° C. crystallize out. The mother liquor is concentrated, and the residue can be re-used for isomerization.

$C_6H_6Br_2O$ (253.9): Calculated: C:28.38; H: 2.38. Found: C: 28.45; H: 2.55.

$^1H$—NMR (CDCl$_3$): = 4.23 (mc, 4,5-H), 5.07 (mc, 3,6-H), 6.17 (mc, 1,2-H).

$^{13}C$—NMR (CDCl$_3$): ppm = 127.3 (C-4,5), 52.0 (C-1,2), 43.3 (C-3,6).

EXAMPLE 5

2,3-Anhydro-1,4-di-O-benzoyl-cyclohex-5-ene-1,2,3,4-tetrols — general instructions 1.27 g (5 mmoles) of the corresponding 1,2-anhydro-3,6-dibromo-cyclohex-4-ene-1,2-diol are dissolved in 30 ml of absolute acetone and 1.07 g (5.5 mmoles) of dry tetramethylammonium benzoate are added. The mixture is stirred for 24 hours at 20° C., the tetramethylammonium bromide which has precipitated is filtered off, the solution is substantially concentrated under reduced pressure, methanol is added and the mixture is left to crystallize at a low temperature. The product is filtered off and washed with a little methanol.

a. (1,2,3,4/0)-2,3-Anhydro-1,4-di-O-benzoyl-cyclohex-5-ene-1,2,3,4-tetrol from (1,2/3,6)-1,2-anhydro-3,6-dibromo-cyclohex-4-ene-1,2-diol.

3.2 g (95%) of colorless crystals, melting point 137°-139° C.

$C_{20}H_{16}O_5$ (336.3): Calculated: C: 71.42; H: 4.80. Found: C: 71.45; H: 5.08.

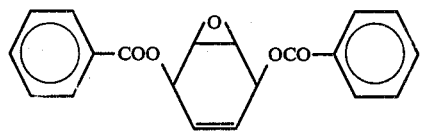

$^1H$—NMR (CDCl$_3$): τ = 1.75-2.06 (m, 4 H), 2.33-2.70 (m, 6 H), 4.00 (mc, 5,6-H), 4.14 (mc, 1,4-H), 6.48 (mc, 2,3-H).

$^{13}C$—NMR (CDCl$_3$): ppm = 166.2 (C=O), 133.5 (para-C), 130.0 (ortho-C), 129.6 (quart.C), 128.5 (meta-C), 125.5 (C-5,6), 67.7 (C-1,4), 51.0 (C-2,3).

b. (1,4/2,3)-2,3-Anhydro-1,4-di-O-benzoyl-cyclohex-5-ene-1,2,3,4-tetrol from (1,2,3,6/0)-1,2-anhydro-3,6-dibromo-cyclohex-4-ene-1,2-diol.

3.3 g (98%) of colorless crystals, melting point 112.5°-114.5° C.

$C_{20}H_{16}O_5$: (336.3) Calculated: C: 71.42; H: 4.80. Found: C: 71.50; H: 5.23.

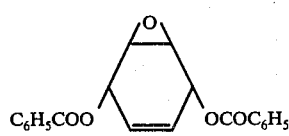

$^1H$—NMR (CDCl$_3$): τ = 1.70-1.97 (m, 4 H), 2.25-2.68 (m, 6 H), 4.07 (mc, 5,6-H), 4.23 (mc, 1,4-H), 6.20 (mc, 2,3-H).

$^{13}C$—NMR (CDCl$_3$): ppm = 165.8 (C=O), 133.5 (para-C), 129.9 (ortho-C), 129.7 (quart.C), 128.5 (meta-C), 125.5 (C-5,6), 64.4 (C-1,4), 50.6 (C-2,3).

c. (1,2,3/4)-2,3-Anhydro-1,4-di-O-benzoyl-cyclohex-5-ene-1,2,3,4-tetrol and (1,2,3/6)-1,2-anhydro-3,6-dibromo-cyclohex-4-ene-1,2-diol.

3.3 g (98%) of colorless crystals, melting point 144.5°-146.5° C.

$C_{20}H_{16}O_5$ (336.3): Calculated: C: 71.42; H: 4.80. Found: C: 71.25; H: 5.08.

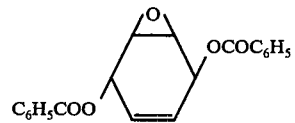

$^1H$—NMR (CDCl$_3$): τ = 1.75-2.04 (m, 4 H), 2.33-2.70 (m, 6 H), 3.93 (mc, 1 H), 4.00-4.30 (m, 3 H), 6.23 (mc, 1 H), 6.40 (mc, 1 H).

$^{13}C$—NMR (CDCl$_3$): ppm = 166.1 (C=O), 165.8 (C=O), 133.5, 130.0, 129.9, 129.6, 128.5 (aromatic-C), 127.6 (C-6), 124.4 (C-5), 67.6 (C-1), 64.8 (C-4), 52.0 (C-3), 51.3 (C-2).

EXAMPLE 6

1,2:4,5-Dianhydro-3,6-dibromo-3,6-didesoxy-cis-inositol from endo, endo-dibromo-epoxy-cyclohexene 2.54 g (10 mmoles) of (1,2,3,5/0)-1,2-anhydro-3,6-dibromo-cyclohex-4-ene-1,2-diol are dissolved in 50 ml of methylene chloride, 5.68 g (40 mmoles) of finely powdered disodium phosphate are added, followed by 15 mmoles of trifluoroperacetic acid added whilst cooling with ice, and the mixture is stirred for 24 hours at 0°-10° C. (Trifluoroperacetic acid is obtained from bis-trifluoroacetic anhydride and 85 percent strength hydrogen peroxide). The solvent is stripped off and the entire residue is thoroughly washed with water, dried and recrystallized from dioxane. 2.2 g (82%) of colorless needles, melting point 225°-227° C., are obtained.

$C_6H_6Br_2O_2$ (269.9): Calculated: C 26.70 H 2.24 Br 59.21. Found: C 26.56 H 2.60 Br 59.11.

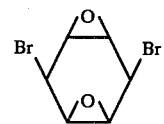

$^1H$—NMR (D$_6$-DMSO): τ = 4.97 (mc, 3,6-H), 6.37 (dd, 1,2,4,5,-H).

$^{13}C$—NMR (D$_6$-DMSO, 90° C.): ppm = 59.4 (1,2,4,C-5), 45.4 (C-3,6).

EXAMPLE 7

(1,2,3,6/0)-1,2-Anhydro-cyclohex-4-ene-1,2,3,6-tetrol 7.0 g (50 mmoles) of anhydrous tetramethylammonium acetate are suspended in 40 ml of anhydrous acetone and 5.0 g (20 mmoles) of 3,6-exo-dibromo-4,5-epoxy-cyclohexene are added whilst stirring. After 5 hours, the tetramethylammonium bromide which has precipitated is filtered off and the filtrate is concentrated on a rotary evaporator. The residue is taken up in 20 ml of methylene chloride and the solution is extracted by shaking with 20 ml of water. After drying the organic phase over MgSO$_4$ and distilling off the solvent on a rotary evaporator, recrystallization of the solid residue from methanol gives the diacetyl compound in the form of colorless crystals of melting point 83° C.

For hydrolysis, the diacetyl compound is taken up in 20 ml of methanol and ammonia is passed in for about 10 minutes. After 12 hours at 20° C., the solvent is distilled off and the crystalline residue is recrystallized from ethyl acetate. Yield, 9.9 g (94%) of melting point 102° C.

$C_6H_8O_3$ (128.1): Calculated: C: 56.85; H: 6.29. Found: C: 56.71; H: 6.41.

$^1$H—NMR ($D_2O$, 60 MHz): $\tau$ = 4.43 (m, 3(4)-H); 5.23 (m, OH); 5.45 (m, 2(5)-H); 6.35 (m, 1(6)-H).

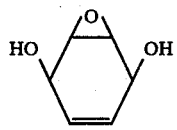

3,6-O-Diacetyl-(1,2,3,6/0)-1,2-anhydro-cyclohex-4-ene-1,2,3,6-tetrol.

Melting point 83° C. (colorless crystals).

$C_{10}H_{12}O_5$ (212.2): Calculated: C: 56.63; H: 5.70. Found: C: 56.44; H: 5.92.

$^1$H—NMR (CDCl$_3$, 60 MHz): $\tau$ = 4.13 (m, 3(4)-H); 4.43 (m, 2(5)-H); 6.66 (m, 1(6)-H); 7.85 (s, CH$_3$).

EXAMPLE 8

(1,2/3,6)-1,2-Anhydro-cyclohex-4-ene-1,2,3,6-tetrol 7.0 g (60 mmoles) of anhydrous tetramethylammonium acetate are suspended in 40 ml of anhydrous acetone and 5.0 g (20 mmoles) of 3,6-endo-dibromo-4,5-epoxy-cyclohexene are added whilst stirring. After 5 hours, the tetramethylammonium bromide which has precipitated is filtered off and the filtrate is concentrated on a rotary exaporator. The residue is taken up in 20 ml of methylene chloride and the solution is extracted by shaking with 20 ml of water. After drying the organic phase over MgSO$_4$ and distilling off the solvent on a rotary evaporator, recrystallization of the residue from methanol gives the diacetyl compound in the form of colorless crystals of melting point 83° C.

The diacetyl compound is hydrolyzed by taking it up in 20 ml of methanol and passing ammonia into the mixture for about 10 minutes. After 12 hours at 20° C., the solvent is distilled off and the crystalline residue is recrystallized from ethyl acetate. Yield: 4.0 g (95%), melting point 104° C.

$C_6H_8O_3$: (128.1): Calculated: C: 56.85; H: 6.29. Found: C: 56.82; H: 6.48.

$^1$H—NMR ($D_2O$, 60 MHz): $\tau$ = 4.16 (m, 3(4)-H); 5.31 (br.s, OH); 5.52 (m, 2(5)-H); 6.53 (m, 1(6)-H).

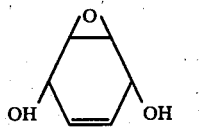

EXAMPLE 9

(1,2/3,6)-1,2-Anhydro-cyclohex-4-ene-1,2,3,6-tetrol 7.0 g (50 mmoles) of anhydrous tetramethylammonium acetate are suspended in 40 ml of anhydrous acetone and 5.0 g (20 mmoles) of 3-endo-6-exo-dibromo-4,5-epoxy-cyclohexene are added whilst stirring. After 5 hours, the tetramethylammonium bromide which has precipitated is filtered off and the filtrate is concentrated on a rotary evaporator. The residue is taken up in 20 ml of methylene chloride and the solution is extracted by shaking with 20 ml of water. After drying the organic phase over MgSO$_4$ and distilling off the solvent on a rotary evaporator, recrystallization of the solid residue from methanol gives the diacetyl compound in the form of colorless crystals of melting point 73° C.

The diacetyl compound is hydrolyzed by taking it up in 20 ml of methanol and passing ammonia into the mixture for about 10 minutes. After 12 hours at 20° C., the solvent is distilled off and the crystalline residue is recrystallized from ethyl acetate. Yield: 3.8 g (91%), melting point 93° C.

$C_6H_8O_3$ (128.1) Calculated: C: 56.85; H: 6.29. Found: C: 56.74; H: 6.14.

$^1$H—NMR ($D_2O$, 60 MHz): $\tau$ = 4.20 (br. m, 3(4)-H); 5.05 (m, OH); 5.35 (m, 2-H); 5.56 (m, 5-H); 6.40 (m, 1(6)-H).

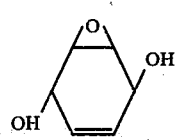

3,6-O-Diacetyl-(1,2,3/6)-1,2-anhydro-cyclohex-4-ene-1,2,3,6-tetrol.

Melting point 73° C. (colorless crystals).

$C_{10}H_{12}O_5$ (212.2): Calculated: C: 56.63; H: 5.70. Found: C: 56.56; H: 5.75.

$^1$H—NMR (CDCl$_3$, 60 MHz: $\tau$ = 4.2 (m, 3(4,2)-H); 4.5 (m, 5-H); 6.41 (m, 1-H); 6.60 (m, 6-H); 7.85 (s, CH$_3$); 7.90 (s, CH$_3$).

EXAMPLE 10

Similar reactions with tetramethylammonium formate, carried out under the conditions described in Examples 7 to 9, give the corresponding diformyl compounds.

a. 3,6,0-Diformyl-(1,2,3,6/0)-1,2-anhydro-cyclohex-4-ene-1,2,3,6-tetrol.

Melting point 87° C.

$C_8H_8O_5$ (184.1): Calculated: C: 52.18; H: 4.38. Found: C: 52.22; H: 4.45.

$^1$H—NMR (CDCl$_3$, 60 MHz): $\tau$ = 1.58 (s, 7(8)-H); 4.25 (m, 3(4)-H); 4.44 (m, 2(5)-H); 6.31 (m, 1(6)-H).

b. 3,6-O-Diformyl-(1,2/3,6)-1,2-anhydro-cyclohex-4-ene-1,2,3,6-tetrol.

Melting point 76° C. (colorless crystals).

$C_8H_8O_5$ (184.1): Calculated: C: 52.18; H: 4.38. Found: C: 52.05; H: 4.60.

$^1$H—NMR (CDCl$_3$, 60 MHz) $\tau$ = 1.80 (s. 8(9)-H); 4.10 (m. 3(4)-H); 4.30 (m, 2(5)-H); 6.61 (m, 1(6)-H).

c. 3,6-O-Diformyl-(1,2,3/6)-1,2-anhydro-cyclohex-4-ene-1,2,3,6-tetrol.

Melting point 85° C. (colorless crystals).

$C_8H_8O_5$ (184.1) Calculated: C: 52.18; H: 4.38. Found: C: 52.11; H: 4.49.

$^1$H—NMR (CDCl$_3$, 60 MHz): $\tau$ = 1.70 (d, 8-H, J = 2 Hz); 1.83 (d, 7-H), J = 2 Hz); 3.9-4.5 (m, 2(3,4,5)-H); 6.40 (m, 1-H); 6.50 (m, 6-H).

EXAMPLE 11

Preparation of trans-benzene trioxide a. 3,6-O-Diacetyl-(1,2/3,6)-1,2-anhydro-cyclohex-4-ene-1,2,3,5-tetrol.

7.0 g (50 mmoles) of anhydrous tetramethylammonium acetate are suspended in 40 ml of anhydrous acetone and 5.0 g (20 mmoles) of 3,6-endo-dibromo-4,5-epoxy-cyclohexene are added whilst stirring. After 5 hours, the tetramethylammonium bromide which has precipitated is filtered off and the filtrate is concentrated on a rotary evaporator. The residue is taken up in 20 ml of methylene chloride and the solution is extracted by shaking with 20 ml of water. After drying the organic phase over MgSO$_4$ and distilling off the solvent on a rotary evaporator, recrystallization from methanol gives colorless crystals. Yield: 4.0 g (96%), melting point 83° C.

C$_{10}$H$_{12}$O$_5$ (212.2): Calculated: C: 56.63; H: 5.70. Found: C: 56.44; H: 5.92.

$^1$H—NMR (CDCl$_3$, 60 MHz): $\tau$ = 4.13 (m, 3(4)-H); 4.43 (m, 2(5)-H); 6.66 (m, 1(6)-H); 7.85 (s, CH$_3$).

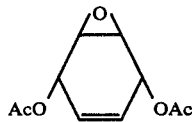

b. 3,6-O-Diacetyl-1,2-anhydro-muco-inositol 10.5 g (50 mmoles) of 3,6-O-diacetyl-(1,2/3,6)-1,2-anhydro-cyclohex-4-ene-1,2,3,6-tetrol are dissolved in 200 ml of ethanol and 50 ml of water. 88 ml of an 0.4 molar aqueous KMnO$_4$ solution, buffered with 5 g of MgSO$_4$, are added dropwise in the course of 4 hours at 0° C., whilst stirring. After completion of the addition, the manganese dioxide which has formed is filtered off and the filtrate is purified, using active charcoal. Thereafter, the filtrate is concentrated to dryness on a rotary evaporator and the solid residue is extracted repeatedly with hot ethyl acetate. Colorless crystals are obtained by recrystallization from ethyl acetate. Yield: 8.0 g (65%), melting point 143° C.

C$_{10}$H$_{14}$O$_7$ (246.1) Calculated: C: 48.78; H: 5.73. Found: C: 48.69; H: 5.66.

$^1$H—NMR (CDCl$_3$/D$_6$-DMSO, 100 MHz): $\tau$ = 4.74 (m, 2(5)-H, J$_{2,3}$+ J$_{2,4}$ = 5 Hz); 5.82 (bd, OH, J = 5 Hz); 6.24 (st, 3(4)-H); 6.82 (bs, 1(6)-H); 7.86 (s, CH$_3$).

$^{13}$C—NMR (CDCl$_3$/D$_6$-DMSO); $\delta$ = 169.92 (CO); 69.68 (2(5)-C); 69.49 (3(4)-C); 53.14 (1(6)-C); 20.92 (CH$_3$).

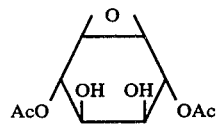

c. 3,6-O-Diacetyl-4,5-O-di-p-toluenesulfonyl-1,2-anhydro-muco-inositol.

6 g (24.4 mmoles) of 3,6-O-diacetyl-1,2-anhydro-muco-inositol are dissolved in 20 ml of absolute pyridine and 10 g (56 mmoles) of tosyl chloride are added whilst cooling with ice. After the mixture has stood for 3 days at 20° C., the reaction is discontinued. To destroy the excess tosyl chloride, about 8 ml of water are added to the solution, whilst cooling with ice. After 1 hour, 50 ml of dilute sulfuric acid are poured into the solution, which is then extracted by shaking with 50 ml of chloroform. The solution is dried over MgSO$_4$ and then purified over a column of 10 g of silica gel, using chloroform as the eluant. After recrystallization from methanol, colorless crystals are obtained. Yield: 12.9 g (96%), melting point 157° C.

C$_{24}$H$_{26}$O$_{11}$S$_2$ (554.5): Calculated: C: 51.97; H: 4.72; S: 11.56. Found: C: 51.72; H: 4.75; S: 11.74.

$^1$H—NMR (CDCl$_3$, 100 MHz): $\tau$ = 2.25 (d, 2'(6')-H, J = 9 Hz); 7.67 (d, 3'(5')-H, J = 9 Hz); 4.70 (m, 1(5)-H, J$_{2,3}$ + J$_{2,4}$ = 5 Hz); 5.25 (m, 3(4)-H); 6.88 (sb, 1(6)-H); 7.76 (s, tos-CH$_3$); 7.97 (s, COCH$_3$).

$^{13}$C—NMR (CDCl$_3$): $\delta$ = 74.27 (3(4)-C); 66.64 (2(5)-C); 52.18 (1(6)-C); 21.71 (tos-CH$_3$); 20.58 (COCH$_3$).

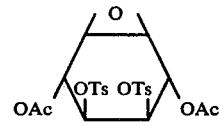

b. 4,5-O-Di-p-toluenesulfonyl-1,2-anhydro-muco-inositol.

12 g (21.6 mmoles) of 3,6-O-diacetyl-4,5-O-di-p-toluenesulfonyl-1,2-anhydro-muco-inositol are taken up in 20 ml of methanol and ammonia is passed in for about 10 minutes. After 24 hours, the hydrolysis has ended. The solvent is stripped off on a rotary evaporator and the solid residue is recrystallized from methanol. Yield: 10 g (99%) of colorless crystals, melting point 192° C.

C$_{20}$H$_{22}$O$_9$S$_2$ (470.5): Calculated: C: 51.05; H: 4.71; S: 13.62. Found: C: 51.15; H: 4.59; S: 13.84.

$^1$H—NMR (CDCl$_3$/D$_6$-DMSO, 100 MHz): $\tau$ = 2.25 (d, 2'(6')-H, J = 9 Hz); 2.68 (d, 3'(5')-H, J = 9 Hz); 4.60 (d, OH, J = 6 Hz); 5.28 (m, 3(4)-H, J$_{2,3}$ + J$_{2,4}$ = 5 Hz); 5.86 (m(5)-H); 6.89 (bs, 1(6)-H); 7.58 (s; CH$_3$).

$^{13}$C—NMR (CDCl$_3$/D$_6$-DMSO): $\delta$ = 78.81 (3(4)-C); 65.45 (1(5)-C); 54.85 (1(6)-C).

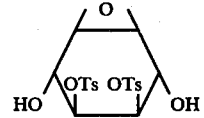

e. 1,2:3,4:5.6-Trisanhydro-allo-inositol ("trans benzenetrioxide")

9.4 g (20 mmoles) of 4,5-di-O-p-toluenesulfonyl-1,2-anhydro-muco-inositol are dissolved in 50 ml of absolute tetrahydrofuran. A mixture of 3.8 g (45 mmoles) of dried monosodium glycollate and 8 g of basic aluminum oxide (activity 1) are added, whilst stirring, to the solution, in such a way that the internal temperature remains at from 15° C. to 25° C. The mixture is stirred for about another hour and is then filtered. The filtrate is concentrated to dryness and is purified over a column of 20 g of silica gel, with methylene chloride as the eluant. The solvent is stripped off on a rotary evaporator and the crystalline residue is recrystallized from methanol. Yield: 2.1 g (85%), melting point 90° C. (colorless needles).

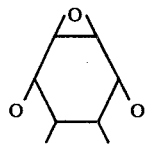

EXAMPLE 12

Preparation of streptamine from cis-benzene-trioxide a. DL-1,2-Anhydro-4,6-biimino-4,6-didesoxy-myo-inositol 2.52 g (20 mmoles) of cis-benzene-trioxide are reacted with 60 ml of molar hydrazine solution at 50° C. in the course of 35 minutes, and the mixture is then rapidly cooled to 0° C. and is extracted with seven 60 ml portions of ice-cold chloroform to remove unreacted cis-benzene-trioxide. The solution is then concentrated to dryness under reduced pressure at below 30° C., ultimately under the vacuum from a diffusion pump. The partially crystalline residue is dissolved or suspended in a small amount of absolute methanol and is left to crystallize at a low temperature (about −20° C.). The product is filtered off, rinsed with a small amount of ice-cold methanol and dried under reduced pressure. It is recrystallized from methanol. 2.50 g (79%) of colorless crystals of melting point about 235° C. are isolated. The mother liquor still contains 17% of product of sufficient purity for reaction with phthalic anhydride.

$C_6H_{10}N_2O_3$ (185.2) Calculated: C: 45.56; H: 6.37; N: 17.71. Found: C: 45.48; H: 6.11; N: 18.24.

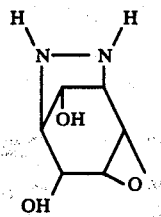

b. DL-1,2-Anhydro-4,6-didesoxy-4,6-[N,N'-(1',2',3',4'-tetrahydro-1',4'-dioxo)-phthalazino]-myo-inositol.

1.58 g (10 mmoles) of DL-1,2-anhydro-4,6-biimino-4,6-didesoxy-myo-inositol are stirred with 1.63 g (11 mmoles) of finely powdered phthalic anhydride in 20 ml of water until reaction is complete. The mixture is then briefly heated at 50° C. and the product is filtered off and washed first with water and then with methanol. 2.80 g (97%) of colorless crystals, melting point about 285° C. (decomposition).

$C_{14}H_{12}N_2O_5$ (288.3): Calculated: C: 58.33; H: 4.20; N: 9.72. Found: C: 58.00; H: 4.64; N: 10.04.

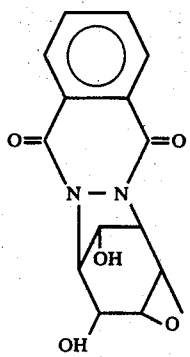

c. 1,3-Didesoxy-1,3-[N,N'-(1',2',3',4'-tetrahydro-1',4'-dioxo)-phthalazino]-scyllo-insositol.

2.88 g (10 mmoles) of DL-1,2-anhydro-4,6-didesoxy-4,6-[N,N'-(1',2',3',4'-tetrahydro-1',4')-phthalazino]-myo-inositol are heated with 0.3 g of phthalic anhydride in 10 ml of water under pressure at 170° C. for 20 hours; on cooling, a hydrate of the phthalazine crystallizes out. The crude product can be purified by recrystallization from water, using active charcoal, and can be obtained analytically pure by drying under reduced pressure at 150° C. 3.00 g (98%) of colorless crystals of melting point about 297° C. (with decomposition) are obtained.

$C_{14}H_{14}N_2O_6$ (306.3): Calculated: C: 54.90; H: 4.61; N: 9.15. Found: C: 54.86; H: 4.75; N: 9.25.

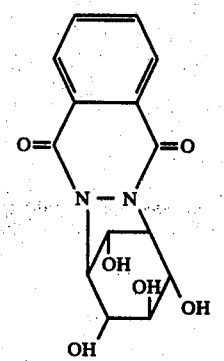

d. Streptamine sulfate.

3.06 g (10 mmoles) of phthalazinedione are heated with 10 ml of 5 molar sodium hydroxide solution for 6 hours at 100° C. in a stream of nitrogen. Hydrogenation with hydrogen in the presence of Raney Ni is then carried out for 24 hours at 20° C. under 10 atmospheres pressure. The catalyst is filtered off, the filtrate is purified with active charcoal and acidified with sulfuric acid, and after adding methanol the product is allowed to crystallize. It is filtered off and washed with 50 percent strength aqueous methanol and then with pure methanol. 1.93 g (70%) are isolated; for purposes of identification, a sample was converted to streptamine hexaacetate by the method described in the literature (R. L. Peck et al., J. Amer. Chem. Soc. 69 (1946), 776), and this product was compared with an authentic sample in respect of its melting characteristics, $^1$H—NMR spectrum and IR spectrum.

EXAMPLE 13

Epistreptamine

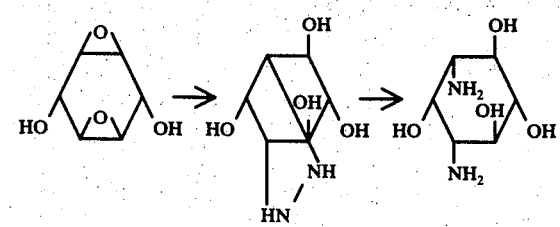

3.0 g (21 mmoles) of (1) are dissolved in 20 ml of $H_2O$ and 2 ml of 80% strength hydrazine monohydrate are added. After heating the mixture for 2 hours under reflux, a reduction to epistreptamine (3) is carried out with Raney nickel and hydrazine. The product is characterized by acetylation with acetic anhydride in pyridine. The yield — the product being in the form of an oil — is 80%, based on (1).

$^1$H—NMR (60 MHz, $CDCl_3$): $\tau$ = 7.74 (1 ax. $COCH_3$), 7.94 (2 eq. $COCH_3$), 7.97 (1 eq. O—$COCH_3$), 8.10 (2 eq. N—$COCH_3$).

EXAMPLE 14

Actinamine

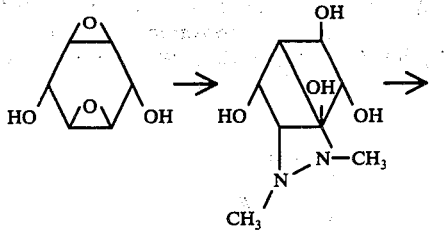

(1)    (2)

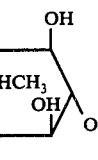

(3)

A solution of 3.0 g (21 mmoles) of (1) and 1.5 g (25 mmoles) of N,N'-dimethylhydrazine in 20 ml of water is boiled under reflux for 3 hours. Compound (2) is reduced to (3) with freshly prepared Raney nickel/hydrazine. The product is characterized by acetylating it with acetic anhydride in pyridine to give the hexaacetate. The yield — the product being in the form of an oil — is 80%, based on (1).

$^1$H—NMR (60 MHz, CDCl$_3$): $\tau$ = 7.17, 7.25 (N—CH$_3$); 7.82, 7.95, 7.99, 8.01 (COCH$_3$).

We claim:

1. A process for increasing the concentration of a particular isomer of 1,4-dibromo-epoxy-cyclohexene in an isomeric mixture of 1,4-dibromo-epoxy-cyclohexenes by establishing a given isomerization equilibrium which comprises;

dissolving said mixture of 1,4-dibromo-epoxy-cyclohexenes in a solvent selected from the group consisting of acetonitrile, methylene chloride, carbon tetrachloride, tetrahydrofuran, benzene, methanol and acetone, acetonitrile being selected as a solvent where the concentration of the endo,endo isomer is to be increased; methylene chloride, carbon tetrachloride, tetrahydrofuran being selected as a solvent where the concentration of the exo,exo isomer is to be increased; and benzene, methanol or acetone being selected as a solvent where the concentration of the endo,exo isomer is to be increased; and allowing the mixture to stand in the presence of a catalytic amount of a soluble bromide salt until said isomerization equilibrium is reached.

2. A process as set forth in claim 1 wherein said soluble bromide salt is a tetraalkylammonium bromide with alkyl radicals of 1 to 5 carbon atoms.

3. A process as set forth in claim 1 wherein said isomeric mixture is dissolved in acetonitrile whereby the concentration of the endo,endo isomer is increased.

4. A process as set forth in claim 1 wherein said isomeric mixture is dissolved in methylene chloride, carbon tetrachloride or tetrahydrofuran whereby the concentration of the exo,exo isomer is increased.

5. A process as set forth in claim 1 wherein said isomeric mixture is dissolved in benzene, methanol or acetone whereby the concentration of the endo,exo isomer is increased.

6. A process as set forth in claim 1 wherein said isomeric mixture of 1,4-dibromo-epoxy-cyclohexenes is obtained by brominating 4,5-epoxy-cyclohexene with N-bromosuccinimide in anhydrous carbon tetrachloride in the presence of a catalytic amount of azobisisobutyronitrile.

* * * * *